(12) United States Patent
He et al.

(10) Patent No.: US 8,663,952 B2
(45) Date of Patent: Mar. 4, 2014

(54) METHOD OF PRODUCING CORN STARCH BY ENZYMATIC PROCESS

(75) Inventors: Xinmin He, Baiyin (CN); Feng Yu, Baiyin (CN); Shuangjing Wang, Baiyin (CN); Qiang Cui, Baiyin (CN); Weiguo Sun, Baiyin (CN)

(73) Assignee: Baiyin Sino Biotechnology Co., Ltd., Baiyin (CN)

( * ) Notice: Subject to any disclaimer, the term of this patent is extended or adjusted under 35 U.S.C. 154(b) by 0 days.

(21) Appl. No.: 13/404,983

(22) Filed: Feb. 24, 2012

(65) Prior Publication Data

US 2012/0288900 A1 Nov. 15, 2012

(30) Foreign Application Priority Data

May 11, 2011 (CN) .......................... 2011 1 0118242

(51) Int. Cl.
*C12P 19/14* (2006.01)

(52) U.S. Cl.
USPC .......................................................... 435/99

(58) Field of Classification Search
None
See application file for complete search history.

(56) References Cited

U.S. PATENT DOCUMENTS

2003/0091691 A1* 5/2003 Olsen et al. ..................... 426/49

FOREIGN PATENT DOCUMENTS

CN 1831013 9/2006
CN 101372702 2/2009

OTHER PUBLICATIONS

"ISI Technical Memorandum on Production of Corn Starch" from International Starch Institute; Science Park Aarhus, Denmark; copyright 1999-2006; retrieved from < http://www.starch.dk/isi/starch/tm18www-corn.htm > on Jul. 10, 2013.*
Sigma-Aldrich Novozymes Catalog product page < http://www.sigmaaldrich.com/life-science/metabolomics/enzyme-explorer/analytical-enzymes/novozymes.html > Retrieved Jul. 11, 2013.*
Saddler et al., "A comparison between the cellulase systems of *Trichoderma harzianum* E58 and *Trichoderma reesei* C30", Appl Microbiol Biotechnol (1985) 22:139-145.*
Ramírez et al., "Enzymatic corn wet milling: engineering process and cost model", Biotechnology for Biofuels 2009, 2:2 (pp. 1-9).*

* cited by examiner

*Primary Examiner* — Suzanne M Noakes
(74) *Attorney, Agent, or Firm* — Colin P. Cahoon; Celina M. Orr; Carstens & Cahoon, LLP

(57) ABSTRACT

A method of producing corn starch by enzymatic process involving: soaking the corn; crushing the corn, separating and washing embryo; fine grinding; washing and drying fiber; separating and drying protein; washing, dewatering and drying the starch. An enzyme preparation is added before the step of washing, dewatering and drying the starch; the enzyme preparation is cellulose, or xylanase, or combination of the cellulose and the xylanase; and addition of the enzyme preparation is from 0.001% to 0.08% by weight of the corn. Based on the technology of traditional wet process, the method of the present invention comprises a step of adding enzyme preparation in the process of separating the corn, which improves the effect and the efficiency of mechanical separation, and further improves the purity and yield of the substance separated while also reducing the energy consumption.

3 Claims, 1 Drawing Sheet

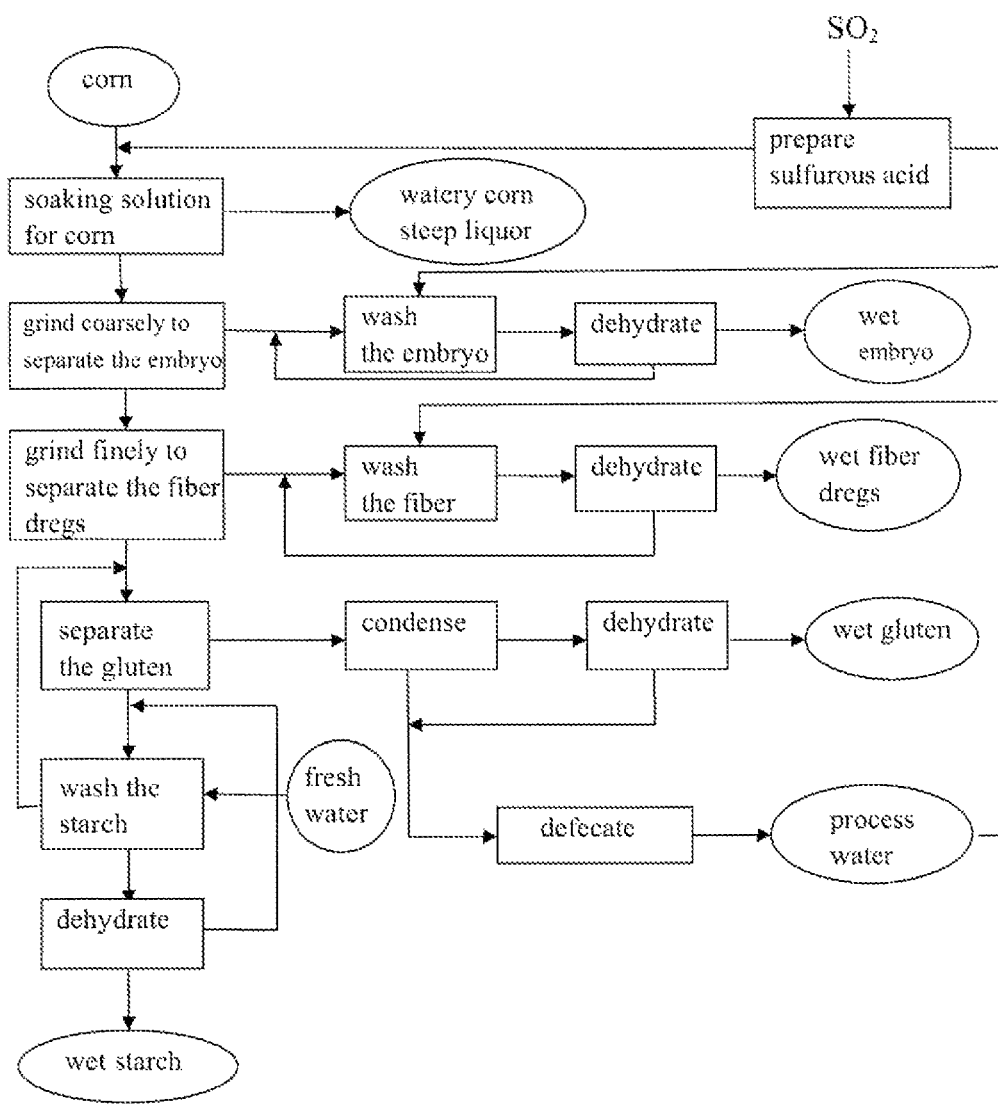

METHOD OF PRODUCING CORN STARCH BY ENZYMATIC PROCESS

TECHNICAL FIELD

The present invention relates to the field of deep processing of corn, specifically, relates to a method of producing corn starch by enzymatic process.

BACKGROUND OF THE INVENTION

Corn starch products are produced from corn grains by the steps of soaking in sulfurous acid, crushing and screening, separating and washing, dehydrating and drying. In addition to direct use in fields of food, paper making, textile, medicine and so on, corn starch is mostly used in deep processing. In China, corn is consumed in a large amount in starch industry. The output of corn starch in China is increasing gradually from 1999 to 2011, which amounted to 21,700,000 tons in 2009, ranking the second in the world. Starch sugar, as a high-end product prepared from corn starch, possesses high economic value and edible value, and is widely used in fields of food, medicine, chemical industry, fermentation and so on. Starch sugar prepared from corn starch includes glucose, fructose, maltose, etc. Corn syrup prepared from corn starch, which is easily assimilated by human body, is a good sweetener for making candies, cakes, beverages and cans. Sorbitol, which is a derivative of starch sugar, is mainly used for producing vitamin C, and there has been high domestic demand for it in recent years. Modified starch is modified on the basis of starch, which is a widely used new product developed in recent years. Over 3000 varieties of modified starch have been developed by foreign countries, but only 50 varieties by China. Modified starch is widely used in fields of paper making, textile, food, feedstuff, medicine, chemical industry, petroleum and so on, with the largest consumption in the fields of paper making, food and textile, and it has promising application prospects. Consequently, the demand of corn starch has been increasing at home and abroad in recent years.

Besides, in addition to the major product of corn starch, four co-products can be obtained in corn starch processing, namely, corn oil, corn fiber, corn gluten meal and corn steep liquor. The corn oil has a content of unsaturated fatty acids over 85%, which mainly includes oleic acid and linoleic acid with an absorption rate over 97% by human body; the corn oil contains sitosterol which could inhibit the increase of cholesterol; and the corn oil is rich in vitamin E which can play a role in cells division in human body and slow down the ageing process. Corn dietary fiber is composed of cellulose and hemicelluloses, which can decrease blood pressure and prevent Heart-Cerebrovascular diseases. The corn gluten meal, as an important co-product in the wet processing of corn, has a content of protein from 50% to 70% and is main material for producing high protein feedstuff and for producing gliadin and other industrial products. The corn steep liquor has a total content of protein from 44% to 48% (dry basis). As a feed formula, the corn steep liquor is a kind of nutriment with high energy and high protein, and is rich in vitamin B and minerals.

Currently, corn starch is commonly processed by wet process in the world. The starch, protein, embryo and fiber in the corn are separated, condensed and dried by mechanical methods such as crushing, screening, centrifugation, squeezing and filtrating and so on. And various methods are adopted by those skilled in the art to improve the processing technology of the corn starch, e.g., a method for shortening the soaking time of corn in corn starch processing was disclosed in Chinese patent publication No. 101372702A, which shortens the soaking time of the corn by soaking the corn under high pressure in combination with complex enzyme. But this method by means of soaking the corn under high pressure goes especially against its application in industrial production, because the process of this method is complex, the cost for the equipment and for the processing is high, and the power consumption is considerable, thus the method for shortening the soaking time of the corn has little practicality in reality. What's more, another method of producing corn starch by means of soaking the corn by enzymatic process was disclosed in Chinese patent publication No. CN1831013A. According to the method, in the first step of soaking, lactobacillus cultivated by fermenting is added to the soaking solution of the corn, and in the third step, proteinase from plant is added to the soaking solution of the crushed corn to degrade proteinaceous matrix so as to release starch, which further shortens the soaking time. In both of the methods disclosed in the patents above, proteinase is added to the soaking solution, but the proteinase will cause some proteins in the corn starch hydrolyzed, finally will result in a loss of the most valuable protein in the corn starch processing. What's more, the soluble protein dissolved in the water will pollute the process water discharged, which is not good for environmental protection. So the separating effect and the purity of the substance separated in the corn starch processing are limited, and the cost for deep processing is high. What's more, power consumptions (water power, electric power and steam power) in the separating process for the substances separated are high, with low efficiency.

SUMMARY OF THE INVENTION

The present invention aims at providing a method of producing corn starch by enzymatic process to overcome the disadvantages in the prior art. Based on the processing technology of traditional wet process, the method of the present invention comprises a step of adding enzyme preparation in the process of separating the corn in order to improve the effect and the efficiency of mechanical separation, and further to improve the purity and the yield of the substance separated. In addition, the method of the present invention can not only improve the yield of the corn starch and the yield of corn gluten meal, but also reduce the energy consumption.

The present invention is achieved by the following technical scheme:

The method of producing corn starch by enzymatic process, comprises steps of: soaking the corn; crushing the corn, separating and washing embryo; fine grinding; washing and drying fiber; separating and drying protein; washing, dewatering and drying the starch, wherein, add enzyme preparation before the step of washing, dewatering and drying the starch; the enzyme preparation is cellulase, or xylanase, or combination of the cellulase and the xylanase; and additive amount of the enzyme preparation is from 0.001% to 0.08% by weight of the corn.

The present invention may be achieved by the following preferred technical schemes:

In the method of producing corn starch by enzymatic process of the present invention, add the enzyme preparation in the step of soaking the corn; or add the enzyme preparation in the step of crushing the corn, separating and washing the embryo; or add the enzyme preparation in the step of washing and drying the fiber.

In the method of producing corn starch by enzymatic process of the present invention, add the enzyme preparation after the step of soaking the corn.

In the method of producing corn starch by enzymatic process of the present invention, add the enzyme preparation in process of washing the embryo during the step of crushing the corn, separating and washing the embryo; or add the enzyme preparation in process of washing the fiber during the step of washing and drying the fiber.

In the method of producing corn starch by enzymatic process of the present invention, add the enzyme preparation in the step of crushing the corn, separating and washing the embryo; and add the enzyme preparation in process of washing the fiber during the step of washing and drying the fiber.

In the method of producing corn starch by enzymatic process of the present invention, add the xylanase in the step of crushing the corn, separating and washing the embryo; and add combination of the cellulase and the xylanase in the process of washing the fiber during the step of washing and drying the fiber.

In the method of producing corn starch by enzymatic process of the present invention, add the enzyme preparation in the step of soaking the corn; add the enzyme preparation in the step of crushing the corn, separating and washing the embryo; and add the enzyme preparation in the process of washing the fiber during the step of washing and drying the fiber.

In the method of producing corn starch by enzymatic process of the present invention, add the cellulase in the step of soaking the corn; add combination of the cellulase and the xylanase in the step of crushing the corn, separating and washing the embryo; and add the xylanase in the process of washing the fiber during the step of washing and drying the fiber.

In the method of producing corn starch by enzymatic process of the present invention, add combination of the cellulase and the xylanase in the step of crushing the corn, separating and washing the embryo; and add the xylanase in the process of washing the fiber during the step of washing and drying the fiber.

In the method of producing corn starch by enzymatic process of the present invention, the enzyme preparation is combination of the cellulase and the xylanase, of which the cellulase accounts for 20% to 40% and the xylanase accounts for 60% to 80% by weight. Preferably, the cellulase accounts for 29% to 31% of the enzyme preparation and the xylanase accounts for 69% to 71% of the enzyme preparation by weight.

In the method of producing corn starch by enzymatic process of the present invention, the cellulase is prepared by *trichoderma reesei* and the xylanase is prepared by *aspergillus niger* under the condition of pH 3.8 to 4.2 and temperature of 50° C. The cellulase and the xylanase both have a half life period of 96 to 144 hours.

In the method of producing corn starch by enzymatic process of the present invention, the enzyme preparation is added along with process water in the steps before the step of washing, dewatering and drying the starch.

The present invention, as compared with the prior art, has the advantages as follows:

The method of the present invention can not only improve the yield of corn starch, but also improve the yield of corn gluten meal. According to the present invention, no protease is added, which prevents the protein from being dissolved, reduces the loss of the most valuable protein in the corn starch processing and reduces the pollution of the soluble protein in the process water discharged.

The cellulase prepared by the *trichoderma reesei* in the present invention has low content of coenzyme and protease, which avoids the increase of soluble substance due to enzymolysis, and reduces the discharge of polluted water, which is benefit to the environment protection. What's more, the decrease of the zymolytic and soluble substance is benefit to improve the effect of separation and the purity of the product.

In the present invention, the enzyme preparation is added while the corn is being crushed or after the corn is crushed. Base on the prior equipment for producing corn starch by wet process, the present invention improves the efficiency of the enzyme preparation without increasing additional power consumptions, reduces the cost of the addition of the enzyme preparation, and improves the effect and the efficiency of mechanical separation; reduces the water consumption for washing and increases the washing efficiency; increases the efficiency of centrifugation, and further reduces the electricity consumption and increases the economic efficiency. The present invention has considerable values in practice.

The enzyme preparation adopted in the present invention has a long half life period, which enables the process water containing enzyme preparation to take effect continuously in the duty-cycle operation, so as to reduce the input cost of the enzyme preparation.

The enzyme preparation in the present invention is the cellulase, or the xylanase, or combination of the cellulase and the xylanase. The present invention takes advantages of the characteristics of the cellulase and the xylanase, which can make the cell walls and the connecting fiber of the corn peel split or separate, to make the cell walls split or fall apart soon, to make the cellulose and the hemicellulose in the corn decompose effectively, and to promote effective separation of the corn peel, the starch in the endosperm, the protein, the embryo and the fiber and so on. According to the present invention, the use of xylanase in combination enables to reduce the hydrophilcity of the cellulose and the hemicelluloses to the utmost, and the content of water in the fiber is reduced, whereby the condensing and drying efficiency is increased, the vapor consumption for condensing and drying is reduced, and then energy consumption is reduced greatly.

BRIEF DESCRIPTION OF THE DRAWING

FIG. 1 is the flow chart illustrating the method of producing corn starch by wet process and the circulation of the process water according to the present invention.

DETAILED DESCRIPTION OF THE PREFERRED EMBODIMENTS

The enzyme preparation in the present invention is cellulase, or xylanase, or a combination of the cellulase and the xylanase. Both the cellulase and the xylanase are products by Baiyin Sino Biotechnology Co., Ltd, which are produced by fermenting under the temperature for survival of the culture as recorded in China Center of Industrial Culture Collection.

A method for preparing cellulase is presented as follows:

Material: *trichoderma reesei* (No. 13051) provided by China Center of Industrial Culture Collection.

Steps:

Preparing slant culture: transfer the *trichoderma reesei* (No. 13051) onto a PDA culture medium slant under sterile conditions; after one to two days of cultivation at temperature of 30° C. and after the slant being all covered, take out and keep the slant culture in cold storage at temperature 4° C. for later use;

Preparing culture of eggplant-shaped bottle slant: transfer the slant culture onto a PDA eggplant-shaped bottle slant under sterile conditions; after one to two days of cultivation at temperature 30° C. and after the eggplant-shaped bottle slant being all covered, take out and keep the culture of the eggplant-shaped bottle slant in cold storage at temperature 4° C. for later use;

Preparing spore suspension: transfer the culture of the eggplant-shaped bottle slant in the ratio of 6% to the inoculation amount into sterile water in a triangular flask of five liters under sterile conditions; transfer the spore suspension in the triangular flask into an inoculation bottle of five liters under sterile conditions;

Extended culture: straw, bran, mineral salt and so on are fed in a culture tank of 6 m³ at a certain ratio; add water to 3 m³ and stir them to mix well; after the mixture is sterilized with steam and its temperature drops to 30~32° C., transfer the spore suspension into the culture tank; after 28 to 36 hours of cultivation under air volume ratio of 1 to 0.2~0.5, temperature of 30~32° C. and tank pressure of 0.05~0.07 Mpa, culture liquor for extended culture is prepared;

Submerged fermenting of the solution: straw, bran, mineral salt and so on are fed in a fermentation tank of 80 m³ at a certain ratio; add water to 50 m³ and stir them to mix well; after the mixture is sterilized with steam and its temperature drops to 30~32° C., the culture liquor for extended culture is cultivated for 98 to 110 hours under the air volume ratio of 1 to 02~0.5, temperature of 30~32° C. and the tank pressure of 0.05~0.08 Mpa to prepare fermented liquor;

Purifying cellulase: solid-liquid separation of the fermented liquor is carried out through polypropylene frame filter to obtain filter residue and clear liquid of cellulase; the clear liquid of cellulase is ultrafiltrated and concentrated by 7 fold with hollow-fiber membranes, of which molecular weight is 10000 Dalton, and then is injected into a storage tank to be dried.

Drying: the concentrated clear liquid of cellulase is dried to obtain powdery cellulase with pressure spray drying tower, of which the inlet temperature is 125~135° C. and the outlet temperature is 60~70° C.;

Standardization: add the powdery cellulase into the starch and other carriers, and they are compounded into the products required;

Finished products: package the compounded products quantitatively and store them in the warehouse.

A method for preparing xylanase is presented as follows:
Material: *Aspergillus niger* (No. 40613) provided by China Center of Industrial Culture Collection.

Steps:
Preparing slant culture: transfer the *aspergillus niger* (No. 40613) onto a PDA culture medium slant under sterile conditions; after one to two days of cultivation at temperature of 30° C. and after the slant being all covered, take out and keep the slant culture in cold storage at temperature of 4° C. for later use;

Preparing culture suspension: transfer the slant culture into a triangular culturing flask of five liters under sterile conditions, in which liquid nutrient medium has been prepared by adding lactose, bran, mineral salt and so on at a certain ratio at PH 5.0~5.8 and by sterilizing; after 36 hours of cultivation at the shaker rotate speed of 180 rpm~200 rpm and temperature of 29~32° C., xylanase culture suspension is prepared for use;

Extended culture: lactose, bran, mineral salt and so on are fed in a culture tank of 6 m³ at a certain ratio; add water to 3 m³ and stir them to mix well; after the mixture being sterilized with steam and its temperature dropping to 29~32° C., transfer the xylanase culture suspension into the culture tank; after 32 to 36 hours of cultivation under the air volume ratio of 1 to 1~1.2, the temperature of 29~32° C., the tank pressure of 0.05~0.07 Mpa and the shaker rotate speed of 180 rpm~300 rpm, culture liquor for extended culture is prepared;

Submerged fermenting of the solution: lactose, bran, mineral salt and so on are fed in a fermentation tank of 80 m³ at a certain ratio; add water to 50 m³ and stir them to mix well; after the mixture is sterilized with steam and its temperature drops to 30~32° C., the culture liquor for extended culture is cultivated for 140 to 150 hours under the air volume ratio of 1 to 1~1.2, the temperature of 29~32° C., the tank pressure of 0.05~0.08 Mpa and the shaker rotate speed of 180 rpm~300 rpm, fermented liquor is prepared;

Purifying xylanase: solid-liquid separation of the fermented liquor is carried out through polypropylene frame filter to obtain filter residue and clear liquid of xylanase; the clear liquid of xylanase is ultrafiltrated and concentrated by 7 fold with hollow-fiber membranes, of which molecular weight is 10000 Dalton, and then is injected into a storage tank to be dried later;

Drying: the concentrated clear liquid of xylanase is dried to obtain powdery xylanase with pressure spray drying tower, of which the inlet temperature is 125~135° C. and the outlet temperature is 60~70° C.;

Standardization: add the powdery xylanase into the starch and other carriers, and they are compounded into the products required;

Finished products: package the compounded products quantitatively and store them in the warehouse.

In the corn starch processing of the present invention, enzyme preparation may be added along with the process water, which is described as follows: dissolve the solid enzyme preparation in 5~10 times of process water; calculate fed-batch volume of the enzyme solution according to flow of the commercial corn in the corn starch processing; the additive amount of enzyme preparation is 0.001~0.08% (based on the weight of the commercial corn). For example, if the flow of the corn is 10 tons per hour and the additive amount of enzyme preparation is 0.01%, namely 1000 grams, then the 10 times of process water is 10 liters, and the fed-batch volume of the enzyme solution is 10 liters per hour.

According to the present invention, the liquid enzyme preparation may alternatively be added directly in the corn starch processing.

As shown in the FIGURE, the working process of the present invention is described in details as follows:

Cleaning Raw Materials

Clear away all kinds of dust, organic and inorganic impurities in the corn. The impurities in the corn must be cleared away to ensure safety in production and quality of the products. The corn is cleaned mainly by screening, air separation and so on. Cleaning equipment includes an oscillating screen, a specific-gravity stoner, a permanent-magnetic tumbler, a barley washer and so on.

Soaking the Corn

The soaking of the corn will have direct influence on the production of the starch in the following steps, that is, have influence on the yield, the quality and quantity of the starch. So soaking the corn is one of the most important steps in the corn starch processing. It aims at changing the structure, chemical and physical properties of endosperm, weakening the bonds in protein and reducing the mechanical strength of the grains, abstracting part of soluble substance and inhibiting the harmful action of microorganisms carried by the corn.

The method of soaking the corn includes still soaking method and countercurrent diffusion soaking method. The still soaking method, in which the soaking solution of different tanks is not transported to each other, is for soaking corn in a single tank. The countercurrent diffusion soaking method is also called diffusion soaking method or multi-tank in series diffusion soaking method. Now the countercurrent diffusion soaking method is widely used in soaking corn by most incorporations. In the countercurrent diffusion soaking method, many soaking tanks, bumps and pipes are connected in series; soaking solution with sulfurous acid is injected directly into the tank in which the corn has been soaked for the longest time (other than in the still soaking method, the soaking solution with sulfurous acid is injected into the tank along with the fresh corn), and after being cycled, the soaking solution is injected by bumps into the soaking tank in which the corn has been soaked for shorter time. In this way, the soaking solution in one tank is injected in turn into another opposite to the feed direction of the fresh corn. The injection of sulfurous acid to the tanks is along an opposite direction to the feeding of the corn, i.e. the decrease of the content of soluble dry matter in the corn along tanks is in an inverse direction to the increase of the content of the soluble dry matter in the soaking solution.

The conditions for soaking the corn in different factories of different places are different due to the different environment in different places. The common operating conditions are as follows: in the soaking solution, the content of sulphur dioxide is about 0.15%~0.2% and pH is 3.5. In the process of soaking, the sulphur dioxide is absorbed by the corn and the content of it reduces gradually, and in the soaking solution discharged eventually, the content of sulphur dioxide is about 0.01%~0.02% and pH is 3.9~4.1; the temperature of the soaking solution is 50~55° C.; the soaking time is 40~60 hours. The conditions for soaking are determined by the quality of the corn. Generally the corn stored for a long time and the flint corn need to be soaked under stronger conditions, i.e. the content of sulphur dioxide and the temperature should be higher, and the soaking time should be longer. The content of water in the corn will be above 40% after soaking.

According to the present invention, the enzyme preparation is added to the soaking solution to make the cell walls and the connecting fiber of the corn peel split or separate, which enables the cellulose and the hemicellulose in the corn to decompose effectively and promotes effective separation of the corn peel, the starch in the endosperm, the protein, the embryo and the fibre and so on.

Crushing the Corn, Separating and Washing the Embryo

After the corn being soaked, physical changes and chemical changes will take place in the corn. Linking bonds between the embryo and the endosperm become weak, and the linking bonds between the protein and the starch in the endosperm of the corn become weak too. The content of water in the embryo of the soaked corn is about 60%, and the embryo of the corn has better elasticity and is separated easily from the corn grains in the process of crushing. Besides, starchiness of the endosperm is partly ground into particles and less than 25% of the starch is released. The crushing of the corn aims at separating the embryo from the endosperm and making a certain amount of starch be released.

Discharge the soaking solution after the corn is soaked, send the corn into a hydrocyclone for sand trap with warm water of 45~50° C. or corn steep liquor to remove the sand, send the corn into a gravity screen to separate the transporting water for recycle, and then the corn is sent into a corn hopper for crushing by crusher. The corn is usually crushed for twice, that is, the corn→the first crushing→the separation of the embryo→the second crushing→the separation of the embryo. Most embryo of the corn is separated from the endosperm after the first crushing and is picked up with a floating tank, and the embryo is completely separated from the endosperm after the second crushing. The embryo separated is transferred on the oscillating screen, and then is sprayed continuously with process water to which enzyme preparation is added in order to wash away the starch milk and gluten which are adhere to the surface of the embryo. The embryo is dehydrated primarily with centrifuge so that the content of water in it is less than 36%.

Fine Grinding and Washing the Fiber

After the corn being crushed and the embryo being separated, the corn contains endosperm granules, gluten, cortices and part of starch granules. Most starch is contained in the endosperm granules and the gluten, and needs finish grinding, so that the starch, the protein and the fiber can be released to the utmost to provide good conditions for the following separation of all ingredients. The object of finish grinding is to destroy the combination of the starch and the non-starch ingredients, to make the starch be dissociated to the utmost, to separate the fiber dregs, to separate the protein in the endosperm from the starch granules, and to make convenience for further separating and refining. The separation of the fiber is to wash for several times the fiber dregs, in which the starch has been released, with process water to which enzyme preparation is added, in order that the fiber dregs contain less dissociated starch and combined starch. The washed fiber will become dry slag crust after being squeezed and dried. The enzyme preparation of the present invention can reduce the hydrophilcity of the cellulose and the hemicellulose to the utmost, and the content of water in the fiber is reduced, whereby the condensing and drying efficiency is increased, the vapor consumption for condensing and drying is reduced, and then energy consumption is reduced greatly.

Separating the Starch and the Protein

The fine starch milk, from which the fiber has been separated, contains a lot of protein, fat, ash content and other non-starch substance in. The protein content is so high that it must be separated from the fine starch milk to get purer starch.

The separation of the starch and the protein is carried out in a butterfly centrifuge. The centrifuge may be adopted to separate the protein from the starch efficiently by, because diameters and specific gravity of the starch granules are greater than those of the protein granules, and sedimentation rate of the starch granules is faster than that of the protein granules.

Washing and Dewatering the Starch Mechanically

In order to remove the soluble protein and the insoluble protein, reduce the acidity of the starch and increase the content of the suspension, the starch is countercurrent washed by fresh process water going through a ten-stage cyclone. After being washed, the starch is dewatered mechanically through a horizontal scraper centrifuge so that the content of water in the wet starch is 38%~40%.

Drying the Starch

Drying is a working procedure for removing the water from the starch by heat energy. The starch is dried by means of pneumatic drying. The drying conditions of drying the starch are controlled as follows: (1) Wind speed is from 14 to 24 m/s, and is generally selected from 17 to 20 m/s. If the wind speed is too low, massive wet piece cannot be taken by the wind and the product is easily damaged by heat; if the wind speed is too high, resistance of the system increases greatly and it is not easy to control the content of water in the product. (2) Blast volume is within the range which can ensure the drier to operate normally when weight ratio of the gas and the solid is from 5 to 10. (3) Drying time is from one to two seconds generally. (4) Air temperature is 140~160° C. (5) Air pressure is used to make up for all kinds of pressure loss of the pneumatic drying pipes.

The content of water in the dried starch is 12~14%. To ensure that fineness of the product is even, sometimes the product will be sorted further. Sift out the starch with specified fineness by screening first, and then the oversize material is sent into the crusher for crushing. Then sift out the starch again to make all the products meet the specified fineness.

The method of producing corn starch by enzymatic process of the present invention will be described in more details with reference to the accompanying embodiments, in order that the aims, the technical scheme and the advantages could be well understood. It should be understood that the embodiments described hereafter are not restricted but intended to explain the present invention.

The First Embodiment:
Production equipment: 1200 tons/day product line for producing corn starch by wet process.

Addition of the enzyme preparation: add enzyme preparation (30% cellulase and 70% xylanase) with the initial additive amount of 0.02%, which is adjusted to 0.015% twenty-four hours later. The point for adding the enzyme preparation is in the process water tank, and the enzyme preparation is added by successive fed-batch for 30 days. In the process of producing corn starch by wet process, raw materials are transferred by process water. Except that the starch is washed with fresh water, the embryo and the fiber are washed with process water. As shown in FIG. 1, the process water may be reused.

Comparison of Data:
Average values obtained during 30 days according to the common method of processing corn by wet process: the yield of starch is 68.6%; the content of amyloid protein is 0.44%; the yield of protein is 4.9%; the vapor consumption is 1.21 tons for each ton of starch; the water consumption is 2.5 tons for each ton of starch; the electricity consumption is 187 kWh per ton; the content of water in the fiber is 66.25%; and the content of the connecting starch in the fiber is 36.87%.

Average values obtained during 30 days according to the method of processing corn by enzymatic process: the yield of starch is 69.7%; the content of amyloid protein is 0.39%; the yield of protein is 5.2%; the vapor consumption is 1.12 tons for each ton of starch; the water consumption is 2.2 tons for each ton of starch; the electricity consumption is 182 kWh per ton; the content of water in the fiber is 61.01%; and the content of the connecting starch in the fiber is 29.34%.

Benefit Analysis:
The yield of starch increases by 1.1%, namely, increase of the yield of starch is 13.2 tons/day (1200 tons/day multiplied by 1.1%), and the direct economic benefit is 42,240 RMB/day (13.2 tons/day multiplied by 3200 RMB/ton) based on the lowest market price of 3200 RMB/ton.

The yield of protein increases by 0.3%, namely, increase of the yield of protein is 3.6 tons/day (1200 tons/day multiplied by 0.3%), and the direct economic benefit is 18,000 RMB/day (3.6 tons/day multiplied by 5000 RMB/ton) based on the lowest market price of 5000 RMB/ton.

The decrease in the vapor consumption is 0.09 ton for each ton of starch, namely, 900 tons of vapor may be saved in processing 10 thousand tons of starch, and the economic benefit is 144000 RMB based on the cost of 160 RMB for each ton of vapor. If the annual output of starch in China is 25 million tons, 2.25 million tons of vapor (which costs 360 million RMB) may be saved.

The decrease in electricity consumption is 5 kWh for each ton of starch, namely, 50000 kWh of electricity may be saved in processing 10 thousand tons of starch, and the economic benefit is 36250 RMB based on the average cost of 0.725 RMB for each kWh of electricity. If the annual output of starch in China is 25 million tons, 125 million kWh of electricity (which costs 90 million RMB) may be saved.

The decrease in water consumption is 0.3 ton for each ton of starch, namely, 3000 tons of water may be saved in processing 10000 tons of starch, and the economic benefit is 10800 RMB based on the average cost of 3.6 RMB for each ton of water. If the annual output of starch in China is 25 million tons, 7.5 million tons of water (which costs 27 million RMB) may be saved.

The Second Embodiment:
Production equipment: 800 ton/day product line for producing corn starch by wet process.

Addition of the enzyme preparation: add enzyme preparation (30% cellulase and 70% xylanase) with the initial additive amount of 0.01%, which is changed to 0.008% forty-eight hours later. The point for adding the enzyme preparation is before fine grinding the corn, and the enzyme preparation is added by successive fed-batch for seven days.

Comparison of Data:
Average values obtained during 7 days according to the common method of processing corn by wet process: the yield of starch is 65.52%; the yield of protein is 4.6%; the vapor consumption is 0.67 tons for each ton of starch; the water consumption is 2.7 tons for each ton of starch; and the electricity consumption is 191 kWh per ton.

Average values obtained during 7 days according to the method of processing corn by enzymatic process: the yield of starch is 66.55%; the yield of protein is 4.76%; the vapor consumption is 0.60 tons for each ton of starch; the water consumption is 2.5 tons for each ton of starch; the electricity consumption is 188 kWh per ton.

The Third Embodiment:
Production equipment: 800 tons/day product line for producing corn starch by wet process.

Addition of the enzyme preparation: add enzyme preparation (30% cellulase and 70% xylanase) with the initial additive amount of 0.01%, which is changed to 0.008% forty-eight hours later. The point for adding the enzyme preparation is when washing the fiber, and the enzyme preparation is added by successive fed-batch for seven days.

Comparison of Data:
Average values obtained during 7 days according to the common method of processing corn by wet process: the yield of starch is 65.52%; the yield of protein is 4.60%; the vapor consumption for drying the fiber is 0.67 tons for each ton of starch; the water consumption is 2.7 tons for each ton of starch; and the electricity consumption is 191 kWh per ton;

Average values obtained during 7 days according to the method of processing corn by enzymatic process: the yield of starch is 66.50%; the yield of protein is 4.74%; the vapor consumption is 0.59 tons for each ton of starch; the water consumption is 2.4 tons for each ton of starch; the electricity consumption is 189 kWh per ton.

The Fourth Embodiment:
Production equipment: 200 tons/day product line for producing corn starch by wet process.

Addition of the enzyme preparation: add the cellulase with the additive amount of 0.01% in the process water tank by successive fed-batch for seven days.

Comparison of Data:
Average values obtained during 7 days according to the common method of processing corn by wet process: the yield of starch is 65.0%; the yield of protein is 4.80%; the vapor consumption for drying the fiber is 0.67 ton for each ton of starch; the water consumption is 2.7 tons for each ton of starch; and the electricity consumption is 191 kWh per ton;

Average values obtained during 7 days according to the method of processing corn by enzymatic process: the yield of starch is 66.5%; the yield of protein is 4.9%; the vapor consumption for drying the fiber is 0.65 ton for each ton of starch; the water consumption is 2.55 tons for each ton of starch; the electricity consumption is 189 kWh per ton.

The Fifth Embodiment:

Production equipment: 200 tons/day product line for producing corn starch by wet process.

Addition of the enzyme preparation: add cellulase with the additive amount of 0.08%, which is changed to 0.01% twelve hours later, in the process water tank by successive fed-batch for seven days. Add xylanase with the additive amount of 0.012% in the step of washing the fiber by successive fed-batch for seven days.

Comparison of Data:

Average values obtained during 7 days according to the common method of processing corn by wet process: the yield of starch is 65.0%; the yield of protein is 4.80%; the vapor consumption for drying the fiber is 0.67 tons for each ton of starch; the water consumption is 2.70 tons for each ton of starch; and the electricity consumption is 191 kWh per ton;

Average values obtained during 7 days according to the method of processing corn by enzymatic processing: the yield of starch is 65.3%; the yield of protein is 4.88%; the vapor consumption for drying the fiber is 0.62 tons for each ton of starch; the water consumption is 2.6 tons for each ton of starch; the electricity consumption is 187 kWh per ton.

The Sixth Embodiment:

Production equipment: 200 tons/day product line for producing corn starch by wet process.

Addition of the enzyme preparation: add cellulase with the additive amount of 0.05%, which is changed to 0.012% twelve hours later, in the step of coarse grinding by successive fed-batch for ten days. Add xylanase with the additive amount of 0.01% in the step of washing the fiber by successive fed-batch for ten days.

Comparison of Data:

Average values obtained during 10 days according to the common method of processing corn by wet process: the yield of starch is 65.0%; the yield of protein is 4.80%; the vapor consumption for drying the fiber is 0.67 tons for each ton of starch; the water consumption is 2.70 tons for each ton of starch; and the electricity consumption is 191 kWh per ton;

Average values obtained during 10 days according to the method of processing corn by enzymatic process: the yield of starch is 65.8%; the yield of protein is 5.0%; the vapor consumption for drying the fiber is 0.60 tons for each ton of starch; the water consumption is 2.4 tons for each ton of starch; the electricity consumption is 185 kWh per ton.

The Seventh Embodiment:

Production equipment: 2000 tons/day product line for producing corn starch by wet process.

Addition of the enzyme preparation: add enzyme preparation (20% cellulase and 80% xylanase) with the additive amount of 0.01% in the water for washing the fiber by successive fed-batch for six days.

Comparison of Data:

Average values obtained during 6 days according to the common method of processing corn by wet process: the soaking time is 59 hours; the quantity of processed corn is 11852 tons; the yield of starch milk is 8259.659 tons; the starch yield is 69.69%; the vapor consumption is 131.2 tons/shift; the content of starch in the fiber is 20.2%; the content of water in the fiber is 59.4%; and the content of protein in the starch milk is 0.42%.

Average values obtained during 6 days according to the method of processing corn by enzymatic process: the soaking time is 52 hours; the quantity of processed corn is 12522 tons; the yield of starch milk is 8858.063 tons; the starch yield is 70.14%; the vapor consumption is 112.7 tons/shift; the content of water in the fiber is 57.5%; and the content of protein in the starch milk is 0.40%.

The Eighth Embodiment:

Production equipment: 2000 tons/day product line for producing corn starch by wet process.

Addition of the enzyme preparation: add enzyme preparation (80% cellulase and 20% xylanase) with the additive amount of 0.01% in the water for washing the embryo by successive fed-batch for 6 days; and add enzyme preparation (20% cellulase and 80% xylanase) with the additive amount of 0.03% in the water for washing the fiber by successive fed-batch for 6 days.

Comparison of Data:

Average values obtained during 6 days according to the common method of processing corn by wet process: the soaking time is 59 hours; the quantity of processed corn is 11852 tons; the yield of starch milk is 8259.659 tons; the starch yield is 69.69%; the vapor consumption is 131.2 tons/shift; the content of starch in the fiber is 20.2%; the content of water in the fiber is 59.4%; and the content of protein in the starch milk is 0.42%.

Average values obtained during 6 days according to the method of processing corn by enzymatic process: the soaking time is 52 hours; the starch yield is 70.35%; the vapor consumption is 117.7 tons/shift; the content of water in the fiber is 58.4%; and the content of protein in the starch milk is 0.40%.

It will be understood by those skilled in the art that the specific additive amount and the adding points are in connection with the capacity of the equipment in use, the conditions, the desired effect and the time for the effect achieved.

It should be explained that the embodiments above of the present invention are just for giving examples and those skilled in the art may make various equivalent changes or modifications without departing from the spirit and scope of the invention. Thus, if the various equivalent changes or modifications of the present invention are made within the scope of the invention and the equivalent technology, the present invention intends to include the equivalent changes or modifications.

What is claimed is:

1. A method of producing corn starch by enzymatic process, comprising steps of:
    soaking corn;
    crushing the corn, separating and washing embryo;
    fine grinding to release starch, protein, and fiber;
    washing and drying the fiber;
    separating and drying the protein; and
    washing, dewatering and drying the starch,
    wherein the method comprises a step of adding enzyme preparation before the step of washing, dewatering and drying the starch; the enzyme preparation is a combination of cellulase and xylanase; and additive amount of the enzyme preparation is from 0.001% to 0.08% by weight of the corn;
    wherein the enzyme preparation is added in the step of crushing the corn, separating and washing the embryo along with water, and the enzyme preparation is added in the process of washing the fiber during the step of washing and drying the fiber along with water.

2. The method of producing corn starch by enzymatic process according to claim 1, wherein the cellulase accounts for 20% to 40% of the enzyme preparation and the xylanase accounts for 60% to 80% by weight of the enzyme preparation.

3. The method of producing corn starch by enzymatic process according to claim 2, wherein, the cellulase accounts for 29% to 31% of the enzyme preparation and the xylanase accounts for 69% to 71% of the enzyme preparation by weight.

\* \* \* \* \*